(12) United States Patent
Dunne et al.

(10) Patent No.: US 8,815,774 B2
(45) Date of Patent: Aug. 26, 2014

(54) HERBICIDAL COMPOSITION AND METHOD OF USE THEREOF

(75) Inventors: Cheryl Dunne, Vero Beach, FL (US); John R James, Greensboro, NC (US)

(73) Assignee: Syngenta Crop Protection LLC, Greensboro, NC (US)

( * ) Notice: Subject to any disclaimer, the term of this patent is extended or adjusted under 35 U.S.C. 154(b) by 0 days.

(21) Appl. No.: 13/597,492

(22) Filed: Aug. 29, 2012

(65) Prior Publication Data
US 2012/0329652 A1 Dec. 27, 2012

Related U.S. Application Data

(63) Continuation of application No. 12/373,952, filed as application No. PCT/US2007/782898 on Jul. 6, 2007, now abandoned.

(60) Provisional application No. 60/807,757, filed on Jul. 19, 2006.

(51) Int. Cl.
*A01N 43/00* (2006.01)
(52) U.S. Cl.
USPC ............................................. 504/139
(58) Field of Classification Search
None
See application file for complete search history.

(56) References Cited

U.S. PATENT DOCUMENTS

| | | | |
|---|---|---|---|
| H0001711 H | * | 2/1998 | Smith, III ..................... 504/136 |
| H1711 H | | 2/1998 | Smith, III |
| 5,935,905 A | * | 8/1999 | Mito .............................. 504/128 |
| 6,455,469 B1 | | 9/2002 | Crosby et al. |
| 6,703,349 B2 | * | 3/2004 | Silverman et al. ............ 504/286 |
| 6,849,579 B2 | * | 2/2005 | Armbruster et al. .......... 504/130 |
| 2002/0039968 A1 | * | 4/2002 | Aven et al. .................... 504/128 |
| 2002/0107148 A1 | | 8/2002 | Crosby et al. |
| 2004/0048746 A1 | | 3/2004 | Cornes |
| 2005/0202972 A1 | * | 9/2005 | Piper et al. .................... 504/190 |

FOREIGN PATENT DOCUMENTS

| | | |
|---|---|---|
| DE | 19919951 A1 | 9/1999 |
| WO | 00/27203 A1 | 5/2000 |
| WO | 0219823 | 3/2002 |
| WO | WO 0219823 * | 3/2002 |

\* cited by examiner

*Primary Examiner* — Alton Pryor
(74) *Attorney, Agent, or Firm* — Brian D. McAlhaney

(57) ABSTRACT

The present invention relates to a to a method of controlling the growth of weeds, in particular, large crabgrass and white clover, using a herbicidal composition comprising mesotrione and a triazolinone herbicide such as sulfentrazone or carfentrazone-ethyl. The invention also relates to the use of this composition.

12 Claims, No Drawings

HERBICIDAL COMPOSITION AND METHOD OF USE THEREOF

This application is a continuation of U.S. application Ser. No. 12/373592 filed Sep. 17, 2009, which is a 371 of International Application No. PTC/US/2007/072898 filed Jul. 6, 2007, which claims priority to U.S. 60/807757 filed Sep. 19, 2006, the contents of which are incorporated herein by reference.

The present invention relates to a herbicidal composition comprising mesotrione and a triazolinone herbicide such as sulfentrazone or carfentrazone-ethyl. The invention also relates to a method of controlling the growth of weeds, in particular large crabgrass and white clover using the composition, and to the use of this composition.

The protection of crops from weeds and other vegetation that inhibit crop growth is a constantly recurring problem in agriculture and turf management. In addition, aesthetically, it may be of interest to remove such unwanted weeds and vegetation, for example, when growing turf in areas such as golf courses, lawns and public parks. To help combat these problems, researchers in the field of synthetic chemistry have produced an extensive variety of chemicals and chemical formulations effective in the control of such unwanted growth. Chemical herbicides of many types have been disclosed in the literature and a large number are in commercial use. Commercial herbicides and some that are still in development are described in 'The Pesticide Manual', 13$^{th}$ Edition, published 2003 by the British Crop Protection Council.

In some cases, herbicidal active ingredients have been shown to be more effective in combination than when applied individually, and this is referred to as "synergism", since the combination demonstrates a potency or activity level exceeding that which it would be expected to have based on knowledge of the individual potencies of the components. The present invention resides in the discovery that mesotrione, or a salt or metal chelate thereof, and sulfentrazone, already known individually for their herbicidal properties, display a synergistic effect when applied in combination.

The herbicidal compounds forming the composition of this invention are independently known in the art for their effects on plant growth. They are disclosed in 'The Pesticide Manual', ibid, and are also commercially available.

Mesotrione (2-(2'-nitro-4'-methylsulphonylbenzoyl)-1,3-cyclohexanedione) is a member of an important class of selective herbicides, the triketones and works by affecting carotenoid biosynthesis. In particular, it inhibits the enzyme 4-hydroxyphenyl-pyruvate dioxygenase (it is an HPPD-inhibitor). In the acid form, its structure can be represented as:

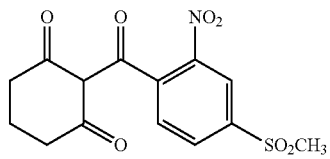 [SMILES: CS(=O)(=O)c1ccc(C(=O)C2C(=O)CCCC2=O)c([N+](=O)[O-])c1]

In addition to the acid form, mesotrione also forms salts and metal chelate, for example, a copper chelate. These metal chelates are disclosed, inter alia, in U.S. Pat. No. 5,912,207 (the disclosure of which is herein incorporated by reference) where they are shown to have unexpectedly superior stability in certain environments when compared to unchelated mesotrione.

Mesotrione is best known for its ability to control a wide spectrum of broadleaf weeds at a wide range of growth stages when applied post-emergence on corn and turfgrass. It is typically used at a low rate (100-225 grams of active ingredient per hectare depending on herbicide formulation on application timing) to control weeds which are present at application and which emerge for up to four weeks afterwards. Once applied, mesotrione is rapidly absorbed by the leaves, shoots, roots and seeds. In susceptible weeds, it disrupts carotenoid biosynthesis, an essential process for plant growth and this leads to plant death. Unlike weeds, corn plants and certain turfgrass species are able to tolerate mesotrione by rapidly breaking down the active compound into inactive compounds.

Triazolinone herbicides are selective herbicides which act by inhibiting photosynthesis. There may be mentioned sulfentrazone, carfentrazone-ethyl, amicarbazone and azafenidin. In particular, there may be mentioned sulfentrazone 2',4'-dichloro-5'-(4-difluoromethyl-4,5-dihydro-3-methyl-5-oxo-1H-1,2,4-triazol-1-yl)methanesulfonanilide. Its structure can be represented as:

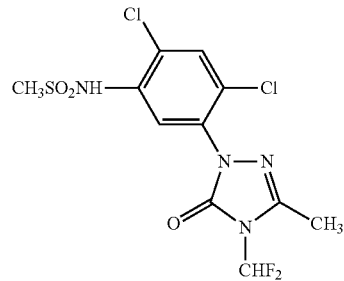

Accordingly, the present invention provides a herbicidal composition comprising a herbicidally effective amount of a mixture of mesotrione and a triazolinone herbicide.

In one embodiment of the invention, the triazolinone herbicide is sulfentrazone, carfentrazone-ethyl, amicarbazone, thiencarbazone or azafenidin. In a particular embodiment, the triazolinone herbicide is sulfentrazone.

The composition contains a herbicidally effective amount of a combination of mesotrione and a triazolinone. The term 'herbicide' as used herein denotes a compound which controls or modifies the growth of plants. The term 'herbicidally effective amount' indicates the quantity of such a compound or combination of such compounds which is capable of producing a controlling or modifying effect on the growth of plants. Controlling or modifying effects include all deviation from natural development, for example: killing, retardation, leaf burn, albinism, dwarfing and the like. For example, plants that are not killed are often stunted and non-competitive with flowering disrupted. The term 'plants' refers to all physical parts of a plant, including seeds, seedlings, saplings, roots, tubers, stems, stalks, foliage and fruits.

It is noted that mesotrione is only one of a number of herbicides that act as HPPD inhibitors. Other HPPD inhibitors are also known and may be used in the composition of the present invention in place of mesotrione. Suitably, other HPPD inhibitors for use in the present invention may be selected from the group consisting of triketones, isoxazoles, pyrazoles, benzobicyclon and ketospiradox. Further details of the individual compounds which fall within the triketones, isoxazoles and pyrazoles may be found in PCT Publication No. WO 2005/053407 (the disclosure of which is herein incorporated by reference) but there may be mentioned sulcotrione, isoxaflutole, isoxachlortole, benxofenap, pyrazolynate and pyrazoxyfen. Further suitable HPPD inhibitors for use in the present invention in place of mesotrione include tembotrione, topramezone, and a compound of the formula

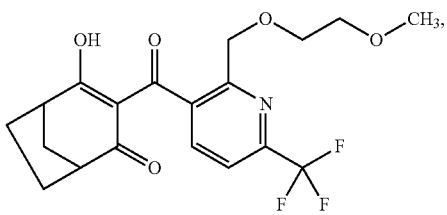 [SMILES: COCCOCc1nc(C(F)(F)F)ccc1C(=O)C1=C(O)C2CCC(C2)C1=O]

As used herein, the designation 'mesotrione' includes the salts and chelated forms of mesotrione as well as the acid form and also includes any enolic tautomeric forms that may give rise to geometric isomers. Furthermore, in certain cases, the various substituents and/or chelated forms may contribute to optical isomerism and/or stereoisomerism. All such tautomeric forms, racemic mixtures and isomers are included within the scope of the present invention.

In one embodiment of the invention, the mesotrione is present as the acid form. In a further embodiment, mesotrione is present as a salt or a metal chelate.

Suitable salts of mesotrione include salts of cations or anions which are known and accepted in the art for the formation of salts for agricultural or horticultural use. Such salts may be formed, for example, using amines, alkali metal bases, alkaline earth metal bases and quaternary ammonium bases.

Metal chelates of 2-(substituted benzoyl)-1,3-cyclohexanedione compounds including mesotrione are described, inter alia, in U.S. Pat. No. 5,912,207. In one embodiment, suitable metal chelates of mesotrione have the general structure:

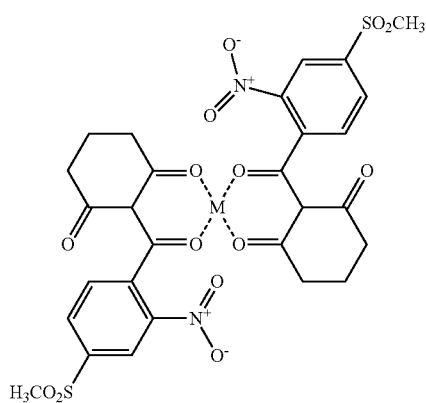

wherein M represents a di- or trivalent metal ion.

Suitably, the di- or trivalent metal ion may be a $Cu^{2+}$, $Co^{2+}$, $Zn^{2+}$, $Ni^{2+}$, $Ca^{2+}$, $Al^{3+}$, $Ti^{3+}$ or $Fe^{3+}$ ion. More suitably, the metal ion may be a divalent transition metal ion such as $Cu^{2+}$, $Ni^{2+}$, $Zn^{2+}$ and $Co^{2+}$. More suitably the metal ion may be $Cu^{2+}$ and $Zn^{2+}$ and most suitably $Cu^{2+}$.

Herbicidal metal chelates of mesotrione for use in this invention may be prepared by the methods described in the aforementioned US Patent, or by the application and adaptation of known methods used or described in the chemical literature. In particular, any appropriate salt which would be a source of a di- or trivalent metal ion may be used to form the metal chelate of the dione compound in accordance with this invention. Particularly suitable salts include chlorides, sulphates, nitrates, carbonates, phosphates and acetates.

Suitably, the compositions of the invention comprise mesotrione and the triazolinone herbicide in a synergistically effective amount. In the compositions of this invention, the weight ratio of mesotrione to the triazolinone herbicide at which the herbicidal effect is synergistic lies within the range of between about 1:100 and about 1:1. Preferably, the weight ratio of mesotrione to triazolinone herbicide is between about 1:100 and about 1:2. More preferably, the weight ratio of mesotrione to triazolinone herbicide is between about 1:50 and about 1:5, with a weight ratio of about 1:12 being especially preferred.

The rate at which the composition of the invention is applied will depend upon the particular type of weed to be controlled, the degree of control required and the timing and method of application. In general, the compositions of the invention can be applied at an application rate of between 0.005 kilograms/hectare (kg/ha) and about 5.0 kg/ha, based on the total amount of active ingredient (mesotrione and triazolinone herbicide) in the composition. An application rate of between about 0.1 kg/ha and about 3.0 kg/ha is preferred, with an application rate of between about 0.12 kg/ha and 1 kg/ha being especially preferred. It is noted that the rates used in the examples below are glasshouse rates and are lower than those normally applied in the field as herbicide effects tend to be magnified in such conditions.

In a further aspect, the present invention provides a method of controlling or modifying the growth of weeds comprising applying to the locus of such weeds a herbicidally effective amount of a composition of the invention.

The composition of the invention may be used against a large number of agronomically important weeds, including, but not limited to, monocotyledonous weeds such as *Agrostis* spp., *Digitaria* spp. (e.g. *D. ischaemum*, *D. sanguinalis*), *Avena* spp., *Setaria* spp., *Lolium* spp., *Echinochloa* spp., *Eleusine* spp. (e.g. *Eleusine indica*), *Scirpus* spp., *Monochoria* spp., *Sagittaria* spp., *Bromus* spp., *Alopecurus* spp., *Sorghum halepense*, *Rottboellia* spp., *Cyperus* spp. (e.g. *Cyperus esculentus*) and dicotyledonous weeds such as *Stellaria* spp., *Nasturtium* spp., *Sinapis* spp., *Solanum* spp., *Phaseolus* spp., *Taraxacum* spp. (e.g. *Taraxacum officinale*), *Trifolium* spp. (e.g. *Trifolium repens*), *Abutilon* spp., *Sida* spp., *Xanthium* spp., *Amaranthus* spp., *Chenopodium* spp., *Ipomoea* spp., *Chrysanthemum* spp., *Galium* spp., *Viola* spp. and *Veronica* spp.

More specifically, among the weeds which may be controlled by the composition of the invention, there may be mentioned monocotyledonous weeds such as grasses (e.g. large and smooth crabgrass, bent grass and nimbleweed) and dicotyledonous weeds such as dandelion, white and red clover, chickweed, henbit, corn speedwell, oxalis, buckhorn and broadleaf plantain, dollar weed, FL pusley, lambsquarters, knotweed, ragweed, wild violets, pigweed and hedge weed. In a particular embodiment, the compositions of the invention may be used to control monocotyledonous weeds such as grasses. Suitably, the grass is large crabgrass.

For the purposes of the present invention, the term 'weeds' includes undesirable crop species such as volunteer crops. For example, in the context of turf grass crops such as on a golf course, creeping bentgrass putting green turf can be considered a 'volunteer' if found in a fairway section where a different variety of grass is being cultivated. The other grasses listed below can, similarly, be considered weeds when found in the wrong place.

The 'locus' is intended to include soil, seeds, and seedlings as well as established vegetation.

The benefits of the present invention are seen most when the pesticidal composition is applied to kill weeds in growing crops of useful plants: such as maize (corn) including field corn, pop corn and sweet corn; cotton, wheat, rice, oats, potato sugarbeet, plantation crops (such as bananas, fruit trees, rubber trees, tree nurseries), vines, asparagus, bushberries (such as blueberries), caneberries, cranberries, flax, grain sorghum, okra, peppermint, rhubarb, spearmint and sugarcane.

'Crops' are understood to also include various turf grasses including, but not limited to, the cool-season turf grasses and the warm-season turf grasses.

Cool season turfgrasses include, for example, bluegrasses (*Poa* L.), such as Kentucky bluegrass (*Poa pratensis* L.), rough bluegrass (*Poa trivialis* L.), Canada bluegrass (*Poa compressa* L.) and annual bluegrass (*Poa annua* L.); bentgrasses (*Agrostis* L.), such as creeping bentgrass (*Agrostis palustris* Huds.), colonial bentgrass (*Agrostis tenius* Sibth.), velvet bentgrass (*Agrostis canina* L.) and redtop (*Agrostis alba* L.); fescues (*Festuca* L.), such as tall fescue (*Festuca arundinacea* Schreb.), meadow fescue (*Festuca elation* L.) and fine fescues such as creeping red fescue (*Festuca rubra* L.), chewings fescue (*Festuca rubra* var. *commutata* Gaud.), sheep fescue (*Festuca ovina* L.) and hard fescue (*Festuca longifolia*); and ryegrasses (*Lolium* L.), such as perennial ryegrass (*Lolium perenne* L.) and annual (Italian) ryegrass (*Lolium multiflorum* Lam.).

Warm season turfgrasses include, for example, Bermudagrasses (*Cynodon* L. C. Rich), including hybrid and common Bermudagrass; Zoysiagrasses (*Zoysia Willd.*), St. Augustinegrass (*Stenotaphrum secundatum* (Walt.) Kuntze); and centipedegrass (*Eremochloa ophiuroides* (Munro.) Hack.).

In addition 'crops' are to be understood to include those crops that have been made tolerant to pests and pesticides, including herbicides or classes of herbicides (and, suitably, the herbicides of the present invention), as a result of conventional methods of breeding or genetic engineering. Tolerance to herbicides means a reduced susceptibility to damage caused by a particular herbicide compared to conventional crop breeds. Crops can be modified or bred so as to be tolerant, for example, to HPPD inhibitors such as mesotrione, EPSPS inhibitors such as glyphosate, or to glufosinate. It is noted that corn is inherently tolerant to mesotrione.

Suitably, the composition of the present invention is useful in controlling the growth of undesirable vegetation by pre-emergence or post-emergence application to the locus where control is desired, depending on the crop over which the combination is applied. In one embodiment, the herbicidal composition of the invention is applied as a pre-emergent application.

The compounds of the invention may be applied either simultaneously or sequentially. If administered sequentially, the components may be administered in any order in a suitable timescale, for example, with no longer than 24 hours between the time of administering the first component and the time of administering the last component. Suitably, all the components are administered within a timescale of a few hours, such as one hour. If the components are administered simultaneously, they may be administered separately or as a tank mix or as a pre-formulated mixture of all the components or as a pre-formulated mixture of some of the components tank mixed with the remaining components.

In practice, the compositions of the invention are applied as a formulation containing the various adjuvants and carriers known to or used in the industry. The compositions of the invention may thus be formulated as granules (and, suitably, as stabilised granules, as described below), as wettable powders, as emulsifiable concentrates, as powders or dusts, as flowables, as solutions, as suspensions or emulsions, or as controlled release forms such as microcapsules. These formulations may contain as little as about 0.5% to as much as about 95% or more by weight of active ingredient. The optimum amount for any given compound will depend on formulation, application equipment and nature of the plants to be controlled.

Wettable powders are in the form of finely divided particles which disperse readily in water or other liquid carriers. The particles contain the active ingredient retained in a solid matrix. Typical solid matrices include fuller's earth, kaolin clays, silicas and other readily wet organic or inorganic solids. Wettable powders normally contain about 5% to about 95% of the active ingredient plus a small amount of wetting, dispersing or emulsifying agent.

Emulsifiable concentrates are homogeneous liquid compositions dispersible in water or other liquid and may consist entirely of the active compound with a liquid or solid emulsifying agent, or may also contain a liquid carrier, such as xylene, heavy aromatic naphthas, isophorone and other non-volatile organic solvents. In use, these concentrates are dispersed in water or other liquid and normally applied as a spray to the area to be treated. The amount of active ingredient may range from about 0.5% to about 95% of the concentrate.

Granular formulations include both extrudates and relatively coarse particles and are usually applied without dilution to the area in which suppression of vegetation is desired. Typical carriers for granular formulations include fertiliser, sand, fuller's earth, attapulgite clay, bentonite clays, montmorillonite clay, vermiculite, perlite, calcium carbonate, brick, pumice, pyrophyllite, kaolin, dolomite, plaster, wood flour, ground corn cobs, ground peanut hulls, sugars, sodium chloride, sodium sulphate, sodium silicate, sodium borate, magnesia, mica, iron oxide, zinc oxide, titanium oxide, antimony oxide, cryolite, gypsum, diatomaceous earth, calcium sulphate and other organic or inorganic materials which absorb or which can be coated with the active compound. Particularly suitable is a fertiliser granule carrier. Granular formulations normally contain about 5% to about 25% active ingredients which may include surface-active agents such as heavy aromatic naphthas, kerosene and other petroleum fractions, or vegetable oils; and/or stickers such as dextrins, glue or synthetic resins. Suitably, the granular formulation may be a stabilised composition which comprises at least one granular substrate material containing at least one metal chelate of mesotrione and a triazolinone herbicide. The granular substrate material can be one of the typical carriers mentioned above and/or can be a fertiliser material e.g. urea/formaldehyde fertilisers, urea, potassium chloride, ammonium compounds, phosphorus compounds, sulphur, similar plant nutrients and micronutrients and mixtures or combinations thereof. The metal chelate of mesotrione and a triazolinone herbicide may be homogeneously distributed throughout the granule or may be spray impregnated or absorbed onto the granule substrate after the granules are formed.

Dusts are free-flowing admixtures of the active ingredient with finely divided solids such as talc, clays, flours and other organic and inorganic solids which act as dispersants and carriers.

Microcapsules are typically droplets or granules of the active material enclosed in an inert porous shell which allows escape of the enclosed material to the surroundings at controlled rates. Encapsulated droplets are typically about 1 to 50 microns in diameter. The enclosed liquid typically constitutes about 50 to 95% of the weight of the capsule and may include solvent in addition to the active compound. Encapsulated granules are generally porous granules with porous membranes sealing the granule pore openings, retaining the active species in liquid form inside the granule pores. Granules typically range from 1 millimetre to 1 centimetre, preferably 1 to 2 millimetres in diameter. Granules are formed by extrusion, agglomeration or prilling, or are naturally occurring. Examples of such materials are vermiculite, sintered clay, kaolin, attapulgite clay, sawdust and granular carbon. Shell o membrane materials include natural and synthetic rubbers, cellulosic materials, styrene-butadiene copolymers, polyacrylonitriles, polyacrylates, polyesters, polyamides, polyureas, polyurethanes and starch xanthates.

Other useful formulations for herbicidal applications include simple solutions of the active ingredients in a solvent in which it is completely soluble at the desired concentration, such as acetone, alkylated naphthalenes, xylene and other organic solvents. Pressurised sprayers, wherein the active ingredient is dispersed in finely-divided form as a result of vaporisation of a low boiling dispersant solvent carrier, may also be used.

Many of these formulations described above include wetting, dispersing or emulsifying agents. Examples are alkyl and alkylaryl sulphonates and sulphates and their salts, polyhydric alcohols; polyethoxylated alcohols, esters and fatty amines. These agents, when used, normally comprise from 0.1% to 15% by weight of the formulation.

Suitable agricultural adjuvants and carriers that are useful in formulating the compositions of the invention in the formulation types described above are well known to those skilled in the art. Suitable examples of the different classes are found in the non-limiting list below.

Liquid carriers that can be employed include water, toluene, xylene, petroleum naphtha, crop oil, acetone, methyl ethyl ketone, cyclohexanone, acetic anhydride, acetonitrile, acetophenone, amyl acetate, 2-butanone, chlorobenzene, cyclohexane, cyclohexanol, alkyl acetates, diacetonalcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethyl formamide, dimethyl sulfoxide, 1,4-dioxane, dipropylene glycol, dipropylene glycol methyl ether, dipropylene glycol dibenzoate, diproxitol, alkyl pyrrolidinone, ethyl acetate, 2-ethyl hexanol, ethylene carbonate, 1,1,1-trichloroethane, 2-heptanone, alpha pinene, d-limonene, ethylene glycol, ethylene glycol butyl ether, ethylene glycol methyl ether, gamma-butyrolactone, glycerol, glycerol diacetate, glycerol monoacetate, glycerol triacetate, hexadecane, hexylene glycol, isoamyl acetate, isobornyl acetate, isooctane, isophorone, isopropyl benzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octyl amine acetate, oleic acid, oleylamine, o-xylene, phenol, polyethylene glycol (PEG400), propionic acid, propylene glycol, propylene glycol monomethyl ether, p-xylene, toluene, triethyl phosphate, triethylene glycol, xylene sulfonic acid, paraffin, mineral oil, trichloroethylene, perchloroethylene, ethyl acetate, amyl acetate, butyl acetate, methanol, ethanol, isopropanol, and higher molecular weight alcohols such as amyl alcohol, tetrahydrofurfuryl alcohol, hexanol, octanol, etc. ethylene glycol, propylene glycol, glycerine, N-methyl-2-pyrrolidinone, and the like. Water is generally the carrier of choice for the dilution of concentrates.

Suitable solid carriers include talc, titanium dioxide, pyrophyllite clay, silica, attapulgite clay, kieselguhr, chalk, diatomaxeous earth, lime, calcium carbonate, bentonite clay, fuller's earth, fertiliser, cotton seed hulls, wheat flour, soybean flour, pumice, wood flour, walnut shell flour, lignin and the like.

A broad range of surface-active agents are advantageously employed in both said liquid and solid compositions, especially those designed to be diluted with carrier before application. The surface-active agents can be anionic, cationic, non-ionic or polymeric in character and can be employed as emulsifying agents, wetting agents, suspending agents or for other purposes. Typical surface active agents include salts of alkyl sulfates, such as diethanolammonium lauryl sulphate; alkylarylsulfonate salts, such as calcium dodecylbenzenesulfonate; alkylphenol-alkylene oxide addition products, such as nonylphenol-C.sub. 18 ethoxylate; alcohol-alkylene oxide addition products, such as tridecyl alcohol-C.sub. 16 ethoxylate; soaps, such as sodium stearate; alkylnaphthalenesulfonate salts, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; and salts of mono and dialkyl phosphate esters.

Other adjuvants commonly utilized in agricultural compositions include crystallisation inhibitors, viscosity modifiers, suspending agents, spray droplet modifiers, pigments, antioxidants, foaming agents, light-blocking agents, compatibilizing agents, antifoam agents, sequestering agents, neutralising agents and buffers, corrosion inhibitors, dyes, odorants, spreading agents, penetration aids, micronutrients, emollients, lubricants, sticking agents, and the like. The compositions can also be formulated with liquid fertilizers or solid, particulate fertiliser carriers such as ammonium nitrate, urea and the like.

An important factor in influencing the usefulness of a given herbicide is its selectivity towards crops. In some cases, a beneficial crop is susceptible to the effects of the herbicide. To be effective, an herbicide must cause minimal damage (preferably no damage) to the beneficial crop while maximizing damage to weed species which infest the locus of the crop. To preserve the beneficial aspects of herbicide use and to minimize crop damage, it is known to apply herbicides in combination with an antidote if necessary. As used here in 'antidote' describes a compound which has the effect of establishing herbicide selectivity, i.e. continued herbicidal phytotoxicity to weed species by the herbicide and reduced or non-phytotoxicity to the cultivated crop species. The term 'antidotally effective amount' describes an amount of an antidote compound which counteracts to some degree a phytotoxic response of a beneficial crop to an herbicide. If necessary or desired for a particular application or crop, the composition of the present invention may contain an antidotally effective amount of an antidote for the herbicides of the invention. Those skilled in the art will be familiar with antidotes which are suitable for use with mesotrione and triazolinone herbicides and can readily determine an antidotally effective amount for a particular compound and application.

In addition, further, other biocidally active ingredients or compositions may be combined with the herbicidal composition of this invention. For example, the compositions may contain, in addition to mesotrione and the triazolinone herbicide, other herbicides, insecticides, fungicides, bactericides, acaracides, nematicides and/or plant growth regulators, in order to broaden the spectrum of activity.

Each of the above formulations can be prepared as a package containing the herbicides together with other ingredients of the formulation (diluents, emulsifiers, surfactants, etc.). The formulations can also be prepared by a tank mix method, in which the ingredients are obtained separately and combined at the grower site.

These formulations can be applied to the areas where control is desired by conventional methods. Dust and liquid compositions, for example, can be applied by the use of power-dusters, broom and hand sprayers and spray dusters. The formulations can also be applied from airplanes as a dust or a spray or by rope wick applications. To modify or control growth of germinating seeds or emerging seedlings, dust and liquid formulations can be distributed in the soil to a depth of at least one-half inch below the soil surface or applied to the soil surface only, by spraying or sprinkling. The formulations can also be applied by addition to irrigation water. This permits penetration of the formulations into the soil together with the irrigation water. Dust compositions, granular compositions or liquid formulations applied to the surface of the soil can be distributed below the surface of the soil by conventional means such as discing, dragging or mixing operations.

The present invention can be used in any situation in which weed control is desired, for example in agriculture, on golf courses, or in gardens. The present invention is particularly suitable for the selective control of weeds such as large crabgrass in turfgrass. Mixtures of mesotrione and a triazolinone herbicide coated on or impregnated in a fertiliser granule are particularly useful.

The following examples are for illustrative purposes only. The examples are not intended as necessarily representative of the overall testing performed and are not intended to limit the invention in any way. As one skilled in the art is aware, in herbicidal testing, a significant number of factors that are not readily controllable can affect the results of individual tests and render them non-reproducible. For example, the results may vary depending on environmental factors, such as amount of sunlight and water, soil type, pH of the soil, temperature and humidity, among others. Also, the depth of planting, the application rate of individual and combined herbicides, the application rate of any antidote, and the ratio of the individual herbicides to one another and/or to an antidote as well as the nature of crops or weeds being tested can affect the results of the test. Results may vary from crop to crop within the crop varieties.

EXAMPLES

Example 1

Control of Large Crabgrass with Mesotrione and Sulfentrazone Applied Pre-emergence A glasshouse trial was carried out. Large crabgrass seeds were sown into standard glasshouse potting mix (1:1 v/v Promix:Vero sand soil) contained in 10 cm square plastic pots. Treatments were replicated three times. Mesotrione (in the form Callisto® 480SE) was applied pre-emergence to large crabgrass (*Digitaria sanguinalis*) at either 12 g ai/ha or 24 g ai/ha with or without sulfentrazone (in the form Authority®). When used, sulfentrazone was applied at a rate of 140 g ai/ha or 280 g ai/ha. The adjuvant system was X-77 at 0.1% v/v in deionised water. 200 litres of herbicide/adjuvant system was used per hectare. General weed control was evaluated at 7 days after treatment (DAT). It is noted that all herbicides were applied at reduced field rates because herbicide effects are magnified in a glasshouse environment. Rates were chosen to give a 50 to 70% level of control with herbicides applied alone as this allows for detection of any synergistic effect when tank mixtures are used.

It is noted that control of large crabgrass with the higher rate of mesotrione alone was too high to allow for detection synergy when mesotrione was mixed with sulfentrazone. The lower rate of mesotrione was therefore used in this analysis. Synergy was observed for a combination of this lower rate of mesotrione with the lower rate of sulfentrazone. Table 1 shows these results. The results were evaluated using the Colby formula. The expected result for (A+B) is (A+B)−(A×B/100) where A and B are the 'observed' results for A and B on their own. Control from the tank mixture is synergistic if the actual result is significantly higher than the expected result (significance based on Student-Newman-Keuls multiple range test).

TABLE 1

| Herbicide | Rate (g ai/ha) | Plus Mesotrione at 12 g ai/ha | |
|---|---|---|---|
| | | Actual | Expected |
| Sulfentrazone | 140 | 100 | 87.0 |

Sulfentrazone provided 75% control of large crabgrass (*Digitaria sanguinalis*) on its own; mesotrione provided 50.0% control at the lower rate. Using the Colby formula and Student-Newman-Keuls multiple range test, synergy was seen at these rates of mesotrione and sulfentrazone.

Example 2

Control of White Clover with Mesotrione and Carfentrazone Applied Pre-emergence

A glasshouse trial was set up as described in Example 1, except using carfentrazone instead of sulfentrazone, *Trifolium repens* (white clover) instead of large crabgrass, and different herbicide rates. The results are given in Table 2.

TABLE 2

| Herbicide | Rate (g ai/ha) | Plus Mesotrione at 25 g ai/ha | | Plus Mesotrione at 50 g ai/ha | |
|---|---|---|---|---|---|
| | | Actual | Expected | Actual | Expected |
| Carfentrazone | 18 | 55 | 50 | 75 | 62 |
| Carfentrazone | 36 | 73 | 49 | 85 | 61 |

Example 3

Control of White Clover with Mesotrione and Carfentrazone Applied Post-emergence A glasshouse trial was set up as described in Example 2, except using applying the mixture post emergence rather than pre-emergence. The results are given in Table 3.

TABLE 3

| Herbicide | Rate (g ai/ha) | Plus Mesotrione at 100 g ai/ha | | Plus Mesotrione at 150 g ai/ha | |
|---|---|---|---|---|---|
| | | Actual | Expected | Actual | Expected |
| Carfentrazone | 18 | 70 | 43 | 93 | 65 |
| Carfentrazone | 36 | 72 | 53 | 93 | 71 |

Although the invention has been described with reference to preferred embodiments and examples thereof, the scope of the present invention is not limited only to those described embodiments. As will be apparent to persons skilled in the art, modifications and adaptations to the above-described invention can be made without departing from the spirit and scope of the invention, which is defined and circumscribed by the appended claims. All publications cited herein are hereby incorporated by reference in their entirety for all purposes to the same extent as if each individual publication were specifically and individually indicated to be so incorporated by reference.

The invention claimed is:

1. A method for controlling or modifying the growth of large crabgrass or white clover present in turfgrass, comprising pre-emergence application of a synergistic herbicidally effective amount of a composition comprising a herbicidally effective amount of a mixture of mesotrione and a triazolinone herbicide to the locus of the large crabgrass or white clover present in turfgrass, wherein the triazolinone herbicide is selected from sulfentrazone, carfentrazone or azafenidin.

2. The method of claim 1, wherein the triazolinone herbicide is sulfentrazone.

3. The method of claim 1, wherein the triazolinone herbicide is carfentrazone.

4. The method of claim 1, wherein the mesotrione is in a chelated form.

5. The method of claim 4, wherein the mesotrione is copper chelate of mesotrione.

6. The method of claim 1, wherein the combined amount of mesotrione and triazolinone herbicide applied to the locus of the weeds is between about 0.005 kg/ha and about 5 kg/ha.

7. The method of claim 6, wherein the combined amount of mesotrione and triazolinone herbicide applied to the locus of the weeds is between about 0.1 kg/ha and about 3 kg/ha.

8. The method of claim 7, wherein the combined amount of mesotrione and triazolinone herbicide applied to the locus of the large crabgrass or white clover is between about 0.15 kg/ha and about 1 kg/ha.

9. The method of claim 1, wherein the weight ratio of mesotrione to triazolinone herbicide is between about 1:100 and about 1:1.

10. The method of claim 9, wherein the weight ratio of mesotrione to triazolinone herbicide is between about 1:100 and about 1:2.

11. The method of claim 10, wherein the weight ratio of mesotrione to triazolinone herbicide is between about 1:50 and about 1:5.

12. The method of claim 1, wherein the mixture is impregnated in or coated on a fertiliser granule.

* * * * *